(12) United States Patent
Anderson

(10) Patent No.: US 10,231,529 B2
(45) Date of Patent: Mar. 19, 2019

(54) NON-ROLL STICK PRODUCT CONTAINERS

(71) Applicant: Raymond G. Anderson, Ankeny, IA (US)

(72) Inventor: Raymond G. Anderson, Ankeny, IA (US)

( * ) Notice: Subject to any disclaimer, the term of this patent is extended or adjusted under 35 U.S.C. 154(b) by 0 days.

(21) Appl. No.: 14/765,717

(22) PCT Filed: Feb. 3, 2014

(86) PCT No.: PCT/US2014/014406
§ 371 (c)(1),
(2) Date: Aug. 4, 2015

(87) PCT Pub. No.: WO2014/121183
PCT Pub. Date: Aug. 7, 2014

(65) Prior Publication Data
US 2015/0366321 A1   Dec. 24, 2015

Related U.S. Application Data

(60) Provisional application No. 61/760,472, filed on Feb. 4, 2013.

(51) Int. Cl.
*A45D 40/06* (2006.01)
*A45D 40/00* (2006.01)
*A61M 35/00* (2006.01)
*A45D 40/02* (2006.01)

(52) U.S. Cl.
CPC .............. *A45D 40/06* (2013.01); *A45D 40/00* (2013.01); *A61M 35/003* (2013.01); *A45D 40/023* (2013.01); *A45D 2040/0018* (2013.01)

(58) Field of Classification Search
CPC combination set(s) only.
See application file for complete search history.

(56) References Cited

U.S. PATENT DOCUMENTS

| | | | |
|---|---|---|---|
| 2,311,719 A * | 2/1943 | White | B65D 51/243 215/304 |
| 2,471,483 A | 7/1949 | Frydlender | |
| 5,215,204 A | 6/1993 | Beck et al. | |
| 6,019,535 A * | 2/2000 | Turner | B43K 23/08 15/428 |
| 6,048,121 A | 4/2000 | Carver | |
| 6,409,403 B1 | 6/2002 | Woos | |
| 7,549,559 B2 | 6/2009 | Conroy et al. | |
| 7,566,185 B2 | 7/2009 | Samuelson et al. | |
| 7,785,028 B2 * | 8/2010 | Cont | B43K 23/12 401/202 |
| 7,798,356 B2 | 9/2010 | Kobayashi et al. | |

* cited by examiner

*Primary Examiner* — David J Walczak
(74) *Attorney, Agent, or Firm* — Zarley Law Firm, P.L.C.

(57) ABSTRACT

Three stick product containers. One has a removable top cap with a crown and a hollow base, such that the top cap can be removed and inserted into the hollow base. The top cap has associated with it a thumb lever push ring to prevent the stick from rolling when laid horizontal. The other container is more suitable, for example, for a lip balm that has a top cap with a living hinge that can be flipped all the way back, inserted into a plug insert hole in the base of the cap, and then the cap is used to support the container in an at rest position to prevent it from rolling.

1 Claim, 4 Drawing Sheets

US 10,231,529 B2

NON-ROLL STICK PRODUCT CONTAINERS

CROSS REFERENCE TO RELATED APPLICATION

This application claims the benefit of U.S. Provisional Application No. 61/760,472 filed Feb. 5, 2013.

BACKGROUND OF THE INVENTION

This invention relates to three distinct types of stick product containers for dispensing stick products such as glue, lip balm, sunscreen, or deodorant. The specific type of product is not limiting. Particularly the invention relates to a stick product container with an improved cap design.

Stick products such as but not limited to those for lip balms, sun screens, deodorants, and glue are known. They generally involve a cylindrical housing, a bottom or a base in one end of the housing and a cap on the other. The product is contained inside and is dispensed by one mechanical means or another when the cap is removed. Some have mechanical mechanisms for twisting the base of the cylinder to push out the stick product, others simply push out. Mechanical mechanisms to urge the product towards the top end of the cylinder are well known and need not be described herein.

A particular problem with such stick product containers is difficulty in removing the cap and/or once the cap is removed the cap is often lost, misplaced, simply left off or rolls away from the user. The container easily rolls away as well. The result is that the product inside of the cylindrical barrel or housing dries making it worthless. The present invention solves this and other problems.

SUMMARY OF THE INVENTION

The present invention relates to three stick product containers. One has a removable top cap with a crown and a hollow base, such that the top cap can be removed and inserted into the hollow base. Preferably the top cap has associated with it a thumb lever push ring to make it easier to remove the lid and prevent the stick from rolling when laid horizontal. Another container is more suitable, for example, for a lip balm that has a top cap with a living hinge that can be flipped all the way back, inserted into a plug insert hole in the base of the cap, and then the cap is used to support the container in an at rest position to prevent it from rolling. Yet another container has a removable cap having a living hinge that can be flipped back and inserted in a hole on the base of the cap.

DETAILED DESCRIPTION OF THE PREFERRED EMBODIMENTS

Figure 1:
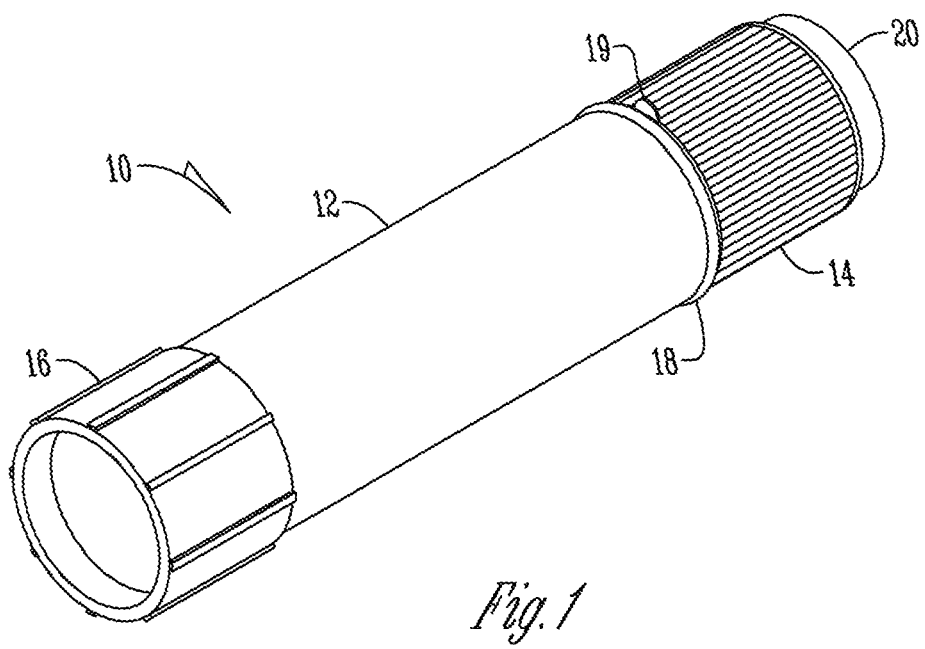
FIG. 1 is a side elevational view of a non-roll stick product container in accordance with the present invention.
Figure 2:
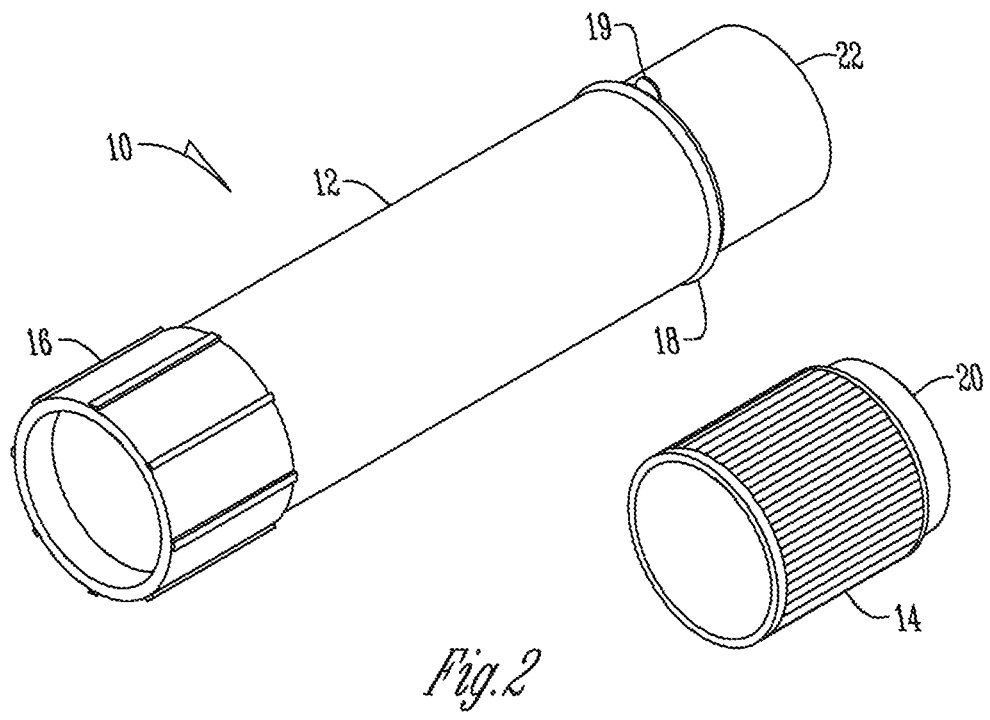
FIG. 2 is a side elevational view with the front (top) cap off.
Figure 3:
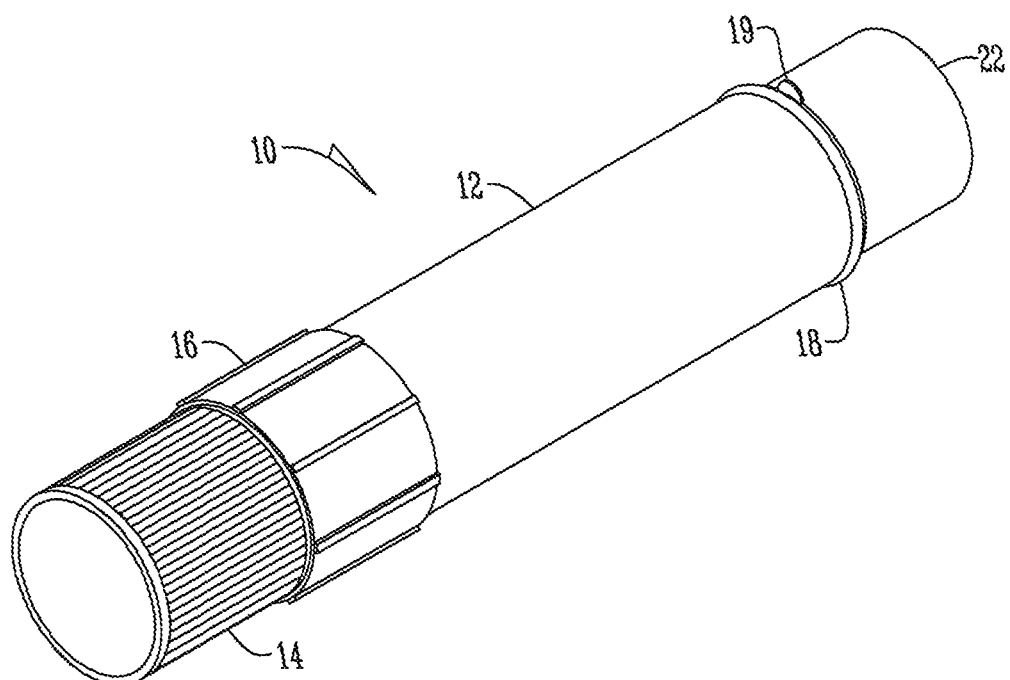
FIG. 3 is a side elevational view with the front cap off and inserted in the hollow bottom so that the container may stand on its own.
Figure 4:
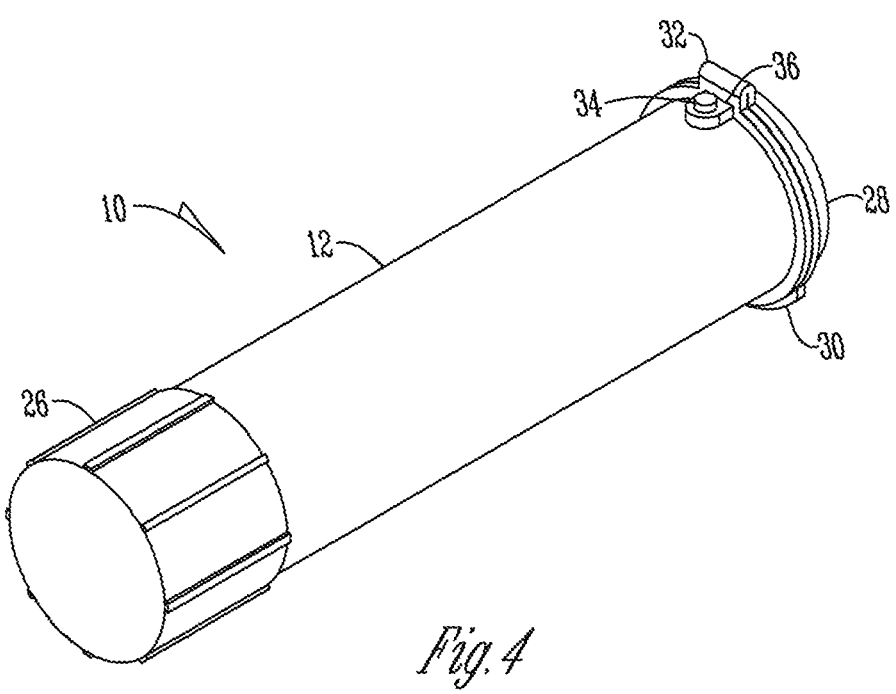
FIG. 4 is a standing view of a non-roll stick product container embodiment of the invention with its flip top cap closed.
Figure 5:
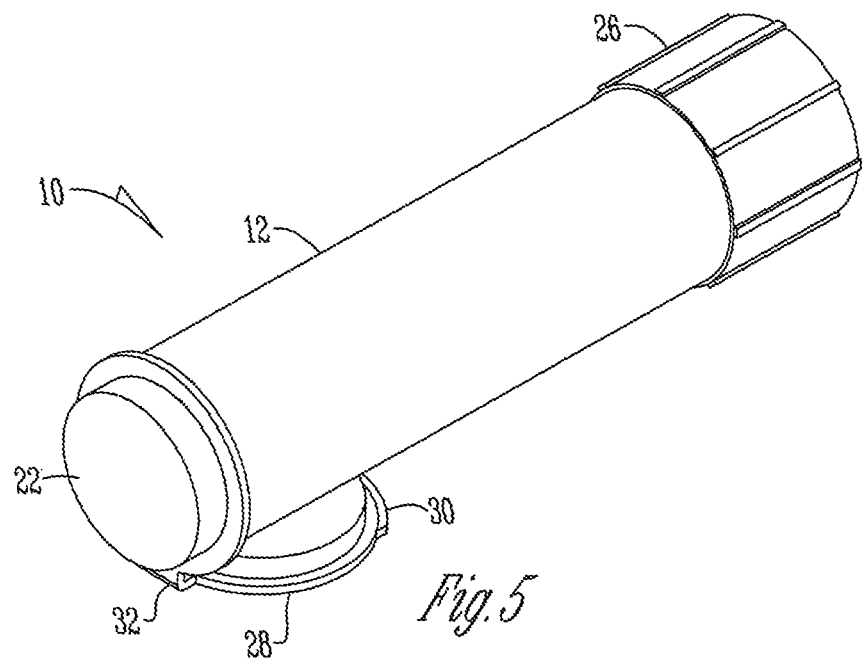
FIG. 5 shows the FIG. 4 container with the flip cap open and in at rest positioned to hold the container in a horizontal position when at rest.
Figure 6:
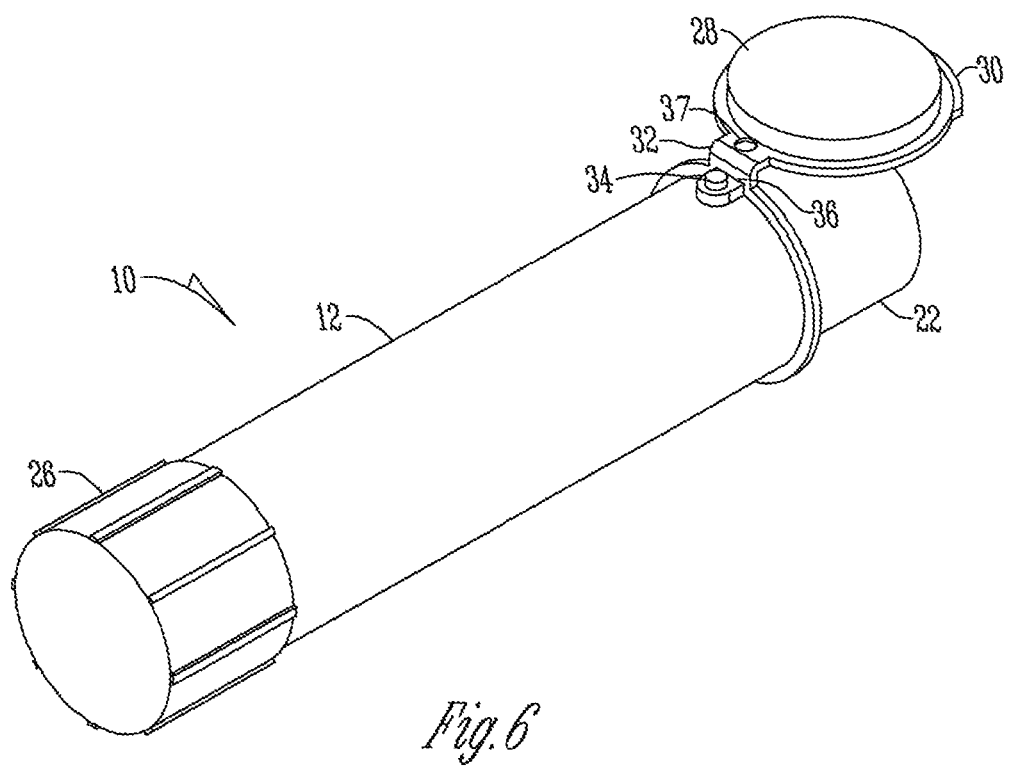
FIG. 6 shows the cap of the non-roll stick container embodiment open and in a standing position to show the living hinge, the plug hole, and the plug of the cap.

Referring now in greater detail to the drawings, first FIGS. 1-3 and then next FIGS. 4, 5, and 6. Stick product container 10 is shown in a close configuration in FIG. 1. Generally, it comprises a cylindrical housing 12, a cap 14 which is removable and a bottom end 16 or base 16 which is non-removable and closes off the end of the cylinder 12. Below the cap 14 and on the cylinder 12 is a push-ring 18. The push ring includes an outwardly extending tab Cap 14 has on its top end a crown 20. The housing 20 may be circular in cross section, oval, rectangular or triangle.

FIG. 2 shows the cap 14 removed to expose the stick product 22. As earlier stated stick product 22 is not a limiting feature of the invention and it may be lip balm, sunscreen, deodorant, glue or other cosmetic, medicinal, or adhesive products. Those skilled in the art know for stick products that lend themselves to a more rigid structure it is typical for the product 10 to have a mechanism to urge the product towards the top end of the cylinder, often operatively engaged by twisting the bottom end or base 16. Such mechanisms are well known and need not be described in detail herein. Push-ring 18 has a thumb lever or tab 19 associated with it which may be pushed up to force the cap to dislodge from product 22 for easy removal. The push ring prevents rolling of the container. Cap 14 has a crown 20 fixed to it in a non-removable manner.

As illustrated in FIG. 3 crown 20 can be inserted into the hollow bottom end or base 16 with the crown 20 matingly fitting into the hollow end of bottom or base 16 so that it removably holds in position. As a result the cap 14 does not fall off or roll around. The product can be kept from rolling by resting on the thumb lever 19 and push-ring 18.

The optional mechanism for moving the product upward when twisting the bottom end or base 16 can be a conventional screw mechanism inside of cylinder housing 12, so that when the cap or base 16 is turned a stick product 22 may advance upwardly, making more product available for use.

Figure 7:
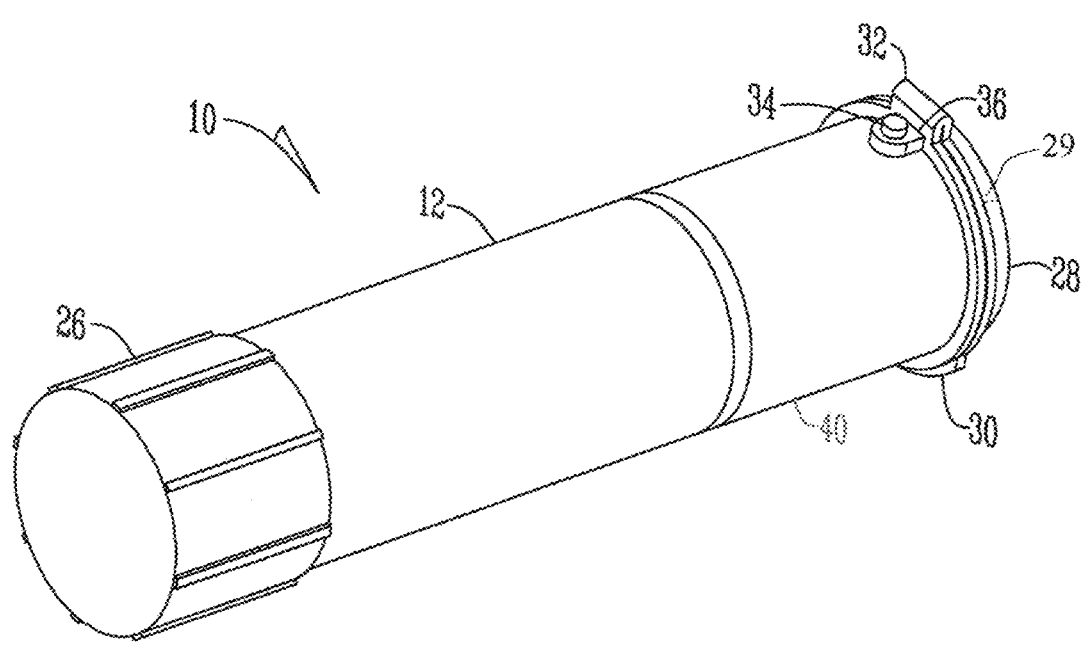
FIG. 7 is a side sectional view of a container and separate flip top cap.

A product dispenser, particularly suitable for a stick product such as lip balm or glue stick is shown in FIGS. 4, 5 and 6. It operates mechanically similarly but has a means of closure. In particular it has similar parts, a cylindrical barrel 12 and a twist base 26, top cap 28 and a thumb release 30, and as well a living hinge 32. The cylinder barrel 12 and flip cap 28 are made of one piece (as in FIG. 4) or multiple pieces (as in FIG. 7). Also, as shown in FIG. 7, the cap 28 may extend outwardly from the cylinder to form a cavity 29 that allows product to remain extended when the cap 28 is closed. Under the living hinge but still on the cap is an insert or lock plug 34. Hinge 32 has an insert base 36 which when thumb release 30 is pushed upwardly and cap 28 moves up and away, then the insert plug 34 fits into the insert hole 37 of hinge 32 and locks it into a rest position shown in FIG. 5 so that the container 10 can rest on cap 28 as depicted in FIG. 5, and also prevent losing the cap or rolling away. Insert lock plug 34 friction fits into insert hole 37 and may simply be pulled out from the same in order to allow the living hinge to function to close the stick product container as needed or desired as shown in closed position in FIG. 6 and opened in a non-rolling at rest position in FIG. 5. In FIG. 4 the cap 28 is attached to the housing 12 by hinge 32. FIG. 7 shows an alternative embodiment where the cap 28 has a collar 40 that snuggly fits around one end of the housing 12. The cap 28 is connected to the collar 40 by hinge 32.

It is to be understood that the preferred embodiments here described are a illustrative only and that the invention is intended to include all the modifications and so far as they come within the scope of the impendent claims or the equivalence thereof.

What is claimed is:

1. A stick product container comprising:
    a housing having a bottom end and an open top end;
    a stick product within the housing;
    a twist base on the bottom end of the housing for urging the product out of the open top end of the housing;
    a cap connected to the housing by a living hinge and movable from a closed position covering the open top end to an open position wherein the open top end is exposed such that the stick product may pass there through wherein the living hinge, the cap and the housing are integrally formed as a one piece unit;
    an insert base protruding from a side surface of the housing adjacent and beneath the living hinge; and
    an insert plug extending from the insert base;
    wherein when the cap is in the open position, the insert plug frictionally engages within a hole in the living hinge to thereby maintain the cap in the open position.

\* \* \* \* \*

UNITED STATES PATENT AND TRADEMARK OFFICE
CERTIFICATE OF CORRECTION

PATENT NO.         : 10,231,529 B2  
APPLICATION NO.    : 14/765717  
DATED              : March 19, 2019  
INVENTOR(S)        : Raymond G. Anderson Page 1 of 1

It is certified that error appears in the above-identified patent and that said Letters Patent is hereby corrected as shown below:

In the Specification

At Column 1, Line 7, delete "5" of the date and substitute "4".

Signed and Sealed this  
Eleventh Day of August, 2020

Andrei Iancu  
*Director of the United States Patent and Trademark Office*